(12) United States Patent
Williams (10) Patent No.: US 7,558,618 B1
(45) Date of Patent: Jul. 7, 2009

(54) METHOD FOR EXTRACTING IMAGES OF VASCULAR STRUCTURE AND BLOOD FLOW FROM IMAGE SEQUENCES

(76) Inventor: Darin S Williams, 11265 E. Chuckwagon Cir., Tucson, AZ (US) 85749

( * ) Notice: Subject to any disclaimer, the term of this patent is extended or adjusted under 35 U.S.C. 154(b) by 518 days.

(21) Appl. No.: 11/327,997

(22) Filed: Jan. 7, 2006

Related U.S. Application Data (60) Provisional application No. 60/644,707, filed on Jan. 18, 2005.

(51) Int. Cl.
*A61B 5/05* (2006.01)
*A61B 6/00* (2006.01)

(52) U.S. Cl. .................. 600/473; 600/407; 600/476

(58) Field of Classification Search ......... 600/473–480, 600/407; 356/51; 250/330–334, 316.1
See application file for complete search history.

(56) References Cited

U.S. PATENT DOCUMENTS

| | | | |
|---|---|---|---|
| 4,947,850 A * | 8/1990 | Vanderkooi et al. ......... 600/431 |
| 5,678,555 A * | 10/1997 | O'Connell .................. 600/479 |
| 6,154,516 A | 11/2000 | Heuscher |
| 6,447,460 B1 | 9/2002 | Zheng |
| 6,501,979 B1 * | 12/2002 | Manning et al. ............ 600/413 |
| 6,539,074 B1 | 3/2003 | Yavuz |
| 6,574,500 B2 | 6/2003 | Keren |
| 6,601,459 B1 | 8/2003 | Jenni |
| 6,620,621 B1 | 9/2003 | Cohenford |
| 6,668,071 B1 | 12/2003 | Minkin |
| 7,359,535 B2 * | 4/2008 | Salla et al. .................. 382/128 |

OTHER PUBLICATIONS

Garbey et al., Estimation of Blood Flow Speed and Vessel Location from Thermal Video, 2004, IEEE, Computer Society Conference on Computer Vision and Pattern Recognition.*

* cited by examiner

*Primary Examiner*—Brian Casler
*Assistant Examiner*—James Kish (57) ABSTRACT

Periodic biological functions and their related anatomy that cannot be seen in image sequences using typical means, can nonetheless be made visible by demodulating the image sequence according to the timing of that biological function using the described method. In particular, vascular structure and the function of that structure becomes observable when demodulated according to the patient's heart beat. This method suppresses the effects of thermal variations across the anatomy, and of severe scattering loss from buried tissues, that limit current thermographic (heat imaging) methods. It also measures localized changes in the wave front amplitude, shape, and phase, which are expected to prove useful for disease diagnosis and biometry.

12 Claims, 8 Drawing Sheets

METHOD FOR EXTRACTING IMAGES OF VASCULAR STRUCTURE AND BLOOD FLOW FROM IMAGE SEQUENCES

This application claims the benefit of provisional patent application No. 60/644,707 filed Jan. 18, 2005.

STATEMENT REGARDING FEDERALLY FUNDED R&D

No federal R&D funds were used in the development of this invention.

REFERENCE TO LIST OR CD APPENDIX

Not applicable.

BACKGROUND OF THE INVENTION

1. Field of Invention

This invention relates to the measurement of biological functions and the related anatomy.

2. Description of Prior Art

Doctors always need better tools for visualizing anatomy and evidences of disease. X-Ray, CT-scans (computer tomographic), MRI (magnetic resonance imaging), and thermography (infra read thermal imaging) serve different niches of this need. Each brings different capabilities. This discussion begins with thermography, as the most relevant of the prior art to the current invention, and then reviews the limited existing applications of time-series imagery in other types of imaging.

Thermographic mammography has drawn interest for detecting breast cancer. It not only avoids the potentially harmful effects of X-ray exposure, but also eliminates the need for squeezing the breast into a position that allows X-rays to bypass the chest wall. It has been suggested that this squeezing may itself contribute to the development of disease. But, the far more relevant risk is that the unpleasantness of the experience prevents many women from seeking adequate screening and diagnosis. The best test in the world is of no use if the patient will not consent to it. A primary benefit of thermography is increasing patient cooperation by eliminating this squeezing.

But existing thermographic techniques are limited by several factors. First, the abnormal vascularization typical of cancer can only be detected indirectly, by local changes in temperature. Thermography senses temperature differences by the relative magnitude of the received infra red (IR) radiation from different areas of the patient. These changes must be found in the presence of the IR emissions from healthy tissues, referred to here as background clutter. As many researchers have discovered, the variations across healthy tissue are so large that is extremely difficult to distinguish them from anomalies due to disease. IR thermography is further complicated by limited tissue penetration due to absorption and scattering of the IR photons emitted from sub-surface tissues. This severely attenuates images of features or problems below the skin surface.

Perhaps the best of the existing thermographic methods for overcoming these problems, due to Dr. George E. Chapman of San Diego, is based on the mammalian "dive" reflex. This reflex causes blood flow to the skin and extremities to shut down under thermal stress, as when sea-based mammals dive into deeper and colder water. This reflex is familiar to skiers as the cause of exaggerated cold in the fingers and toes, relative to the rest of the body.

Chapman uses the dive reflex constructively by placing the patient in a cold room and collecting a baseline thermogram (infra red image). Then, additional thermal stress is applied by placing the patient's hand in ice water. Another thermogram is taken under this stress. The difference between these thermograms shows the degree of dive reflex response. In healthy tissue, the response is severe.

However, this dive response is severely attenuated by the presence of cancer. The chemicals which cause angiogenesis (blood vessel growth) in cancer also attenuate the dive reflex. This attenuation occurs over an extended volume of tissue, so that deeply buried tumors can be detected by observing the skin surface. Lack of the usual dive response indicates cancer.

Thermal variations in healthy tissue are doubly suppressed by this method. First, they are suppressed by chilling the patient, decreasing the overall background clutter level. They are further suppressed by looking at the difference between the baseline thermogram and the stress thermogram. Common spatial features in the background cancel. This removes most of the clutter due to contrasts in healthy tissue.

While this method has proven quite useful for cancer detection, the very nature of the observed phenomena makes it less adequate for localization and for finding other anomalies. It is good for detecting tumors, but other techniques are then needed to determine their exact location and size. And, while the discomfort to the patient is far less than with conventional X-ray approaches, the cold room and icy finger baths are still unpleasant.

And, regardless of this method's effectiveness, it looks for only one phenomenon. It uses only still images, from before and after the thermal stress (the significance of this limitation is developed in the following discussion). A proper diagnostic arsenal contains multiple methods based upon different phenomenologies. Additional methods that detect different characteristics of disease are always sought.

Others have taken different approaches to suppressing background clutter. Most are based on different variations on the theme of subtracting a reference background. Sclager (U.S. Pat. Nos. 4,186,748 and 4,310,003) limits the effect of IR background levels and variations in healthy tissue by examining thermal difference between the patient's left and right breasts. The principle is that disease anomalies tend to be highly asymmetrical compared to normal tissue. This method uses pairs of images taken under static conditions.

Use of temporal (time series) sequences to suppress random noise is well established in the prior art. However, this is not by itself, useful for suppressing clutter that is essentially static over time, which is the problem discussed here.

Zheng, et al (U.S. Pat. No. 6,447,460) looks for static characteristics, such as thermal shading, to find deep vein thrombosis (blood clots). This method looks for anomalies without using baseline image differencing, and uses only still images. It works because it is looking for pronounced thermal differences relative to the background clutter.

Cohenford (U.S. Pat. No. 6,620,621) uses an active illumination rather than passive imaging, looking for specific absorption characteristics vs. wavelength to identify anomalies. A time series of images is used, but this is strictly for the purposes of forming a spectrogram, assessing differences in absorption vs. wavelength for different parts of the tissue as the stimulation varies with time. It looks only for static, not time changing, characteristics of the tissue. These techniques are typically not useful in vivo. And again, no attempt is made to use temporal characteristics of the disease process.

Jenni (U.S. Pat. No. 6,601,459) and variety of other ultrasound solutions use Doppler in order to directly detect localized blood flow. But there still is no attempt to use temporal variations due to disease processes. While Doppler does represent motion, the velocity is used as a static feature, like intensity in a thermogram. No attempt is made to characterize time varying parameters across the image.

Keren, (U.S. Pat. No. 6,574,500) makes very limited use of time series imagery, but for a completely different purpose. Keren looks at a sequence of images to find the most stable sample, by finding the image most like the images sampled near it. This is done to suppress temporal changes, not to highlight them. Selecting the most stable frame provide the greatest difference vs. a later image taken after a contrast agent is injected. Temporal variation is only used as a diagnostic signature in terms of before and after the agent is injected, again comparing two static conditions. This general trend of attempting to suppress temporal variations is repeated elsewhere. Time series data is used only to avoid variations, not to capitalize upon them.

Heuscher, et al (U.S. Pat. No. 6,154,516) and Yavuz, et al. (U.S. Pat. No. 6,539,074) deal with temporal image variations primarily as an impediment to computer tomographic (CT) imaging. They use CT image samples synchronized to the phase of the patient's heartbeat to suppress motion variation/smear, thereby to produce crisp images. Heuscher focuses on creating an image at a single phase of the heartbeat, in order to cancel unintended motion.

Yavuz further suggests the possibility of examining the 3D motion sequence of the heart pumping as a diagnostic tool. But, this still is in the context of watching a moving object. Prior art does not discuss extracting specific temporal features from fixed localized areas.

Minkin (U.S. Pat. No. 6,668,071) explicitly uses temporal variations in an image to find a patient's pulse. But, only in terms of detecting the pulse as a global phenomenon across the image, in much the same sense that a stethoscope measures a single value versus time. No attempt is made to sense localized variations in the temporal response.

SUMMARY

In accordance with the present invention, images of a patient are demodulated according to reference timing derived from a periodic biological function of the patient. This demodulation causes spatial distributions of function and anatomy relating to this biological function to become visible, where they otherwise would not be visible using the same imaging sensor, thereby enhancing utility for disease diagnosis and other applications.

In different embodiments the reference can be a separately measured input to the process, encoded so that it is captured by the imaging sensor without interfering with the above process, or inferred directly from the un-augmented imagery.

OBJECTS AND ADVANTAGES

The fundamental new, unobvious, and unexpected, concept is that periodic biological phenomena and the related anatomy that cannot be seen in imagery using typical means, can nonetheless be made visible in the same imagery by demodulating individual image areas according to the timing of that biological function. In particular, vascular structure and the function of that structure becomes observable when demodulated according to the patient's heart beat.

Conventional wisdom does not regard such effect as observable. Most typically this is because no one thought about there being an effect to observe (the universal response of everyone that the inventor has queried). On deeper thought, most believe (in the absence of evidence), that the modulation depths due to these phenomena would be considerably below the level of the background clutter. That is, they would be lost in the normal spatial variations across the patient's body. However, experience from a different area of radiometry indicates that this would not be a problem.

In calibrating the absolute radiometric response of an infrared sensor in a high background or severe attenuation test-range environment it is typical to use a chopped source. This source may consist of a rotating chopper wheel in front of a conventional black body thermal source. The signal is then measured using a lock-in amplifier or equivalent, suppressing both the non-modulating background and noise that is not in the band of the chopped signal.

The fundamental novel, unobvious, and unexpected observation here is that the heart beat, or other periodic biological phenomenon, provides the same effect as a chopper wheel: it modulates the signal of interest relative to the background. While heart-beat related image variations generally are not observable on a frame by frame basis, the periodic nature of the modulation allows one to reveal them with suitable processing, in the same way that a lock-in amplifier detects a modulating point source even when the random noise is far larger than the signal.

The concept of looking for temporal variations separately across two-dimensionally distributed areas of a patient is also quite novel, producing unexpected benefits. It is notably absent from the prior art.

This is not surprising, since there is substantial historical momentum to direct thinking away from it (teaching against). Using time series to suppress noise, to detect or allow for motion, or to build three-dimensional models of moving or changing objects is well within our usual experience, from X-rays and fluoroscopes forward. Building 3D models from 2D images is no different, cognitively, from what you do looking out a window. But all of these are look for static properties at a single point on an object, they do not infer meaning from how that point changes over time.

Inferring meaning from one dimensional time series is well within typical experience. Consider the stethoscope. But this same one-dimensional thinking has stuck when applying temporal techniques to images (as discussed in the following). Part of the novelty here is bringing these two disparate concepts together.

The method discussed here makes three subtle but substantial deviations from the prior art. These produce strikingly non-obvious benefits.

The first fundamental distinction made here, is that the objective is not to represent or suppress motion, but rather to highlight temporal variations in intensity at individual points on the patient's body. The objective is not, for example, to follow a moving heart behind the chest wall, but rather to determine how the thermal radiation from a particular spot on a blood vessel varies over the pulse cycle. In this manner the hear beat is used to enhance the related anatomy. Temporal changes become an asset to be exploited, rather than a liability to be suppressed.

The second fundamental distinction is producing a spatial map of such modulations. Detecting overall pulse is relatively common, for example to reject non-living counterfeits in biometrics. However, this is a single spatial point measurement over time. In essence, it is the same though process used for hundreds of years in the stethoscope and its predecessors. Measuring differences in temporal variation across and image is a new and unique idea.

The third fundamental distinction is that a single timing reference is used to decode all of the points imaged on the patient. This produces fundamentally different behavior than simply Fourier Transforming points in the image sequence over time (a process which is not documented as producing useful results for such applications). The method taught here focuses the result directly on the biological function of interest. This is particularly true in cases where the function of interest has somewhat unstable timing.

BRIEF DESCRIPTION OF DRAWINGS

Closely related figures and reference numerals have the same number but different alphabetic suffixes.

REFERENCE NUMERALS IN DRAWINGS 120 patient
122 sensor
124 signal encoder
126 source
128 camera
130 image sequence
132 decoder
134 demodulator
136 blood vessels or vascularization
138 map
140 visualization system or V-system
142 visualization device or V-device
144 arm
146 FOV
148 source encoded output
152 input interface
154 output interface
156 timing reference
158 signal from the patient
160 user interface
162 memory
164 combined processing unit
166 display mapping
168 monitor
200 collect the image sequence
202 identify the timing reference
202B alternative 1 identify the timing reference
202C alternative 2 identify the timing reference
204 select the source area
206 detect transitions
208 measure frame relative phase
210 track patient motion
212 select sample areas
214 for each area
216 average pixels
218 create composite
220 remove constant part
222 smooth
224 characterize the modulation
226 acquire image sequence
228 store the data
230 retrieve the data
232 build spatial map
234 assign colors
236 display result
238 encode the synchronization
240 V-method
242 measure the biological function timing or measure the sync
244 encode the timing
246 output the encoding
248 process on-line
250 collect intensities
252 demodulate
256 construct output
280 capture the reference
282 synchronize to images
284 determine timing
290 select body area
292 average the reference
294 evaluate the frequency content
296 select the reference frequency
298 determine the reference
300 input pulse
302 pulse waveform graph
304 rising edge detect
306 toggle output
308 timing marks
310 encoded signal graph
312 frequency transform 1
314 frequency transform 2
316 pulse frequency graph
318 encoded signal frequency graph
320 alignment lines
400 pulse graph
404 phasing marks
406 frame timing marks
408 absolute timing arrow
410 relative timing arrow
412 input intensity graph
416 composite waveform
418 modulating part
420 smoothed waveform
500 feature extraction
502 non-modulating map
504 baseline map
506 augmented map
508 classification
510 further augmented map
512 map of the opposite side of the patient's body
514 sample related portion
516 a priori data

DETAILED DESCRIPTION

Out of graphical necessity, some of the drawings show specific choices from within the much broader scope covered by the following description and claims. In particular, the elements shown are consistent with infra red measurement of a patient's pulse. These selections are to be construed as illustrative, not as limiting beyond the full range of the following discussion and claims.

Figure 1A:
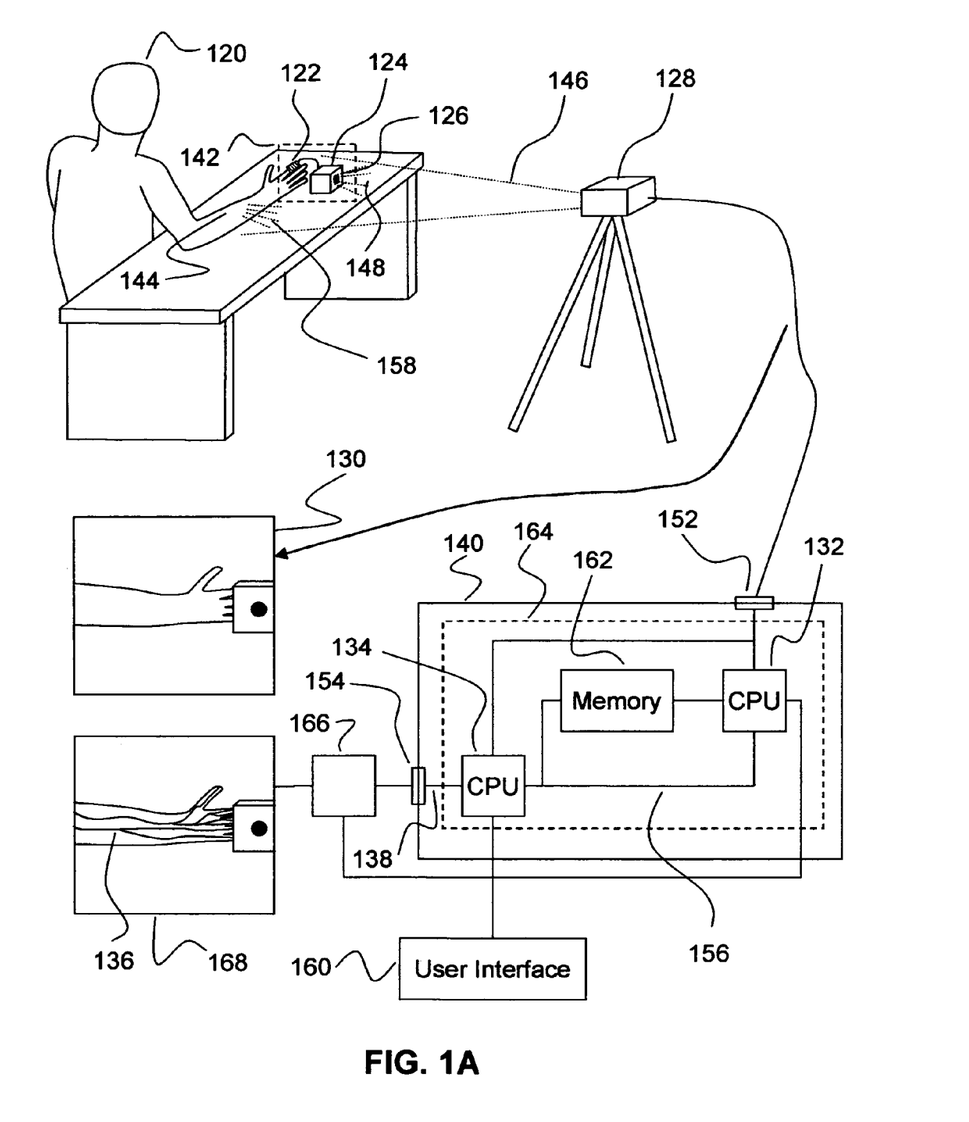
FIG. 1A shows a top level overview of components and interconnections in the preferred embodiment.

FIG. 1A—Overview

Figure 2A:
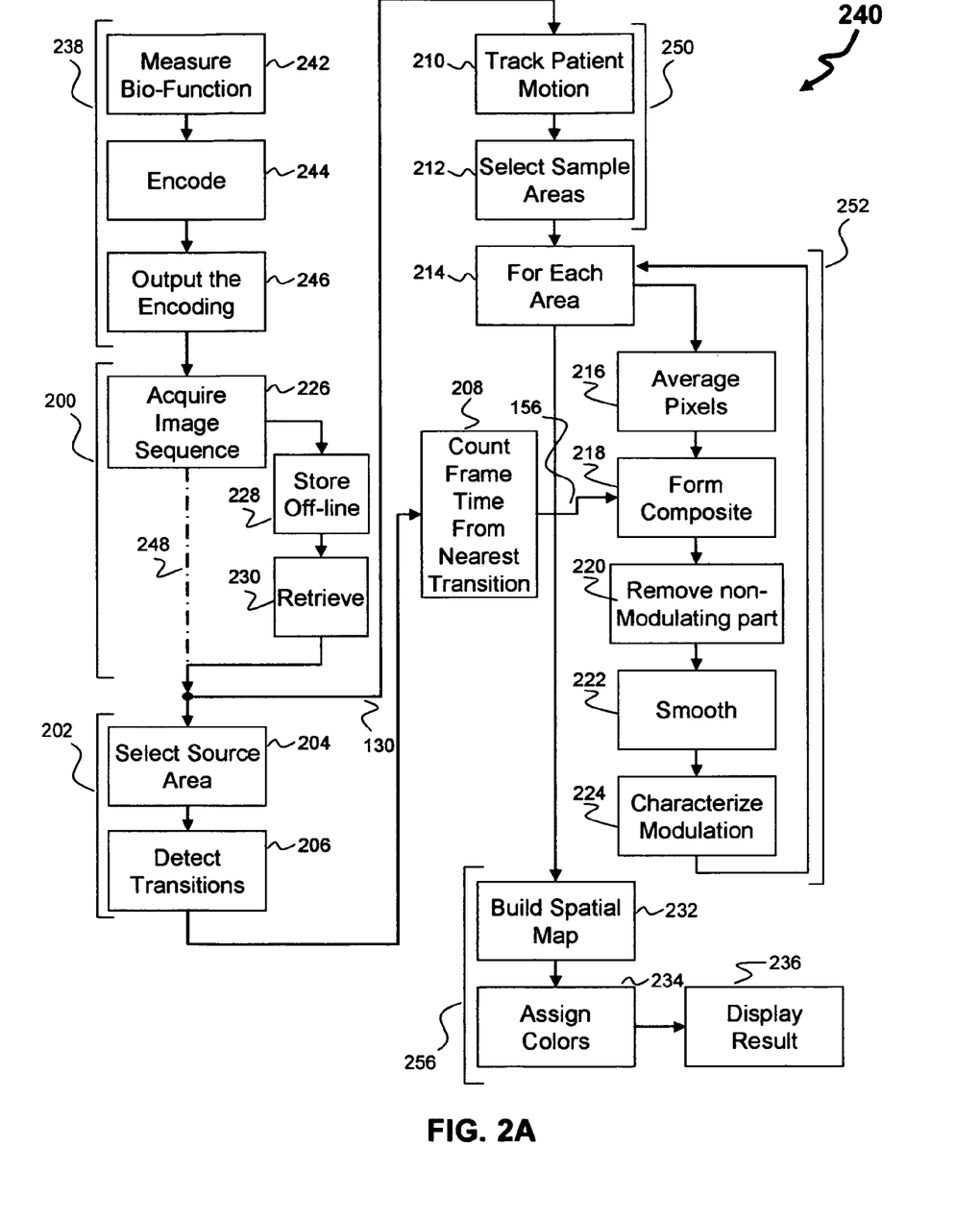
FIG. 2A details the process steps of the preferred embodiment.

FIG. 1A illustrates a top-level overview of the preferred embodiment of the visualization system or V-system 140 and visualization synchronization device or V-device 142, as configured to implement the preferred embodiment of the visualization method or V-method (FIG. 2, 240). This illustration is most consistent with infra red imaging using a heart-beat as the reference, but this choice is illustrative, not restrictive.

A living subject or patient 120 is observed by imaging equipment or a camera 128, so that some part of the patient's body, here an arm 144, is within the camera field of view or FOV 146. This produces a raw image sequence, set of images, or image sequence 130.

A reference sensor or sensor 122 measures a periodic biological function of the patient 120. In this example, the sensor 122 is substantially in contact with the patient 120, but this is not to be construed as limiting. Sensors which do not require body contact may equivalently be used.

The sensor 122 feeds into to a signal encoder 124 which creates an encoded signal, whereby the timing of the original measurement from the patient can be extracted from this encoding. This signal is applied to the attached signal source or source 126.

This source 126 is placed within the FOV 140 of the camera so that it may be seen while imagery of the patient 120 is captured. The source 126 and encoding is constructed, particularly in choice of waveband and temporal content, so that the source encoded output 148 is visible to the camera 128.

The camera 128 directly observes the patient 120 in order to measure modulations occurring in time with the biological function measured by the reference sensor 122. For want of a better term, let us refer this modulating phenomenon which the camera 128 senses as the signal from the patient 158. Note however, that "signal" in this context does not imply a volitional act. The term furthermore is intended to include phenomena sensed by a variety of passive and active imaging equipment, as applied in each particular context.

The source encoded output 148 may be further constructed to be nominally orthogonal, mathematically, to the signal from the patient 158 as captured directly by the camera 128, so that it does not interfere with the signal from the patient 158. This provides, in effect, an independent input channel through the camera 128.

The image sequence 130 from the camera 128 is passed via an input interface 152 to a reference processor or decoder 132. The decoder 132 extracts the timing data placed into the images by the V-device 142, thereby producing a timing reference signal or timing reference 156.

This timing reference 156 feeds, along with the image sequence 130, into the demodulation processor or demodulator 134 which produces a spatial map or map 138. This map shows the local presence in different portions of the image of signals from the patient 158. The spatial map 138 is itself a useful end result. It may also be provided through an output interface 154 for manual inspection or automated analysis.

The reference processor 132, demodulation processor 156, and shared memory 162, need not be separate hardware components. They may equivalently be implemented as functions within a single computer or combined processing unit 164. The description here includes, by inference, this and other equivalent substitutions.

In the example shown, the map 138 is supplied to a processor providing conventional sorts of tools for displaying multivariate two-dimensional data mapping, or display mapping 166, onto an attached monitor 168, controlled via a user interface 160. The objective of this invention is not to provide a specific display mapping method suitable for all applications, but rather to derive an image or map which reveals information which would otherwise remain hidden when using typically sorts of tools. This image is, by itself, a novel and useful result.

When suitably displayed, the map highlights not only the specific biological function but also the related phenomena and anatomy. The map shown here, consistent with infra-red measurement of the patient's 120 pulse, shows blood vessels or vascularization 136 which otherwise would remain hidden by spatial variations in the images of the image sequence 130.

Figure 1B:
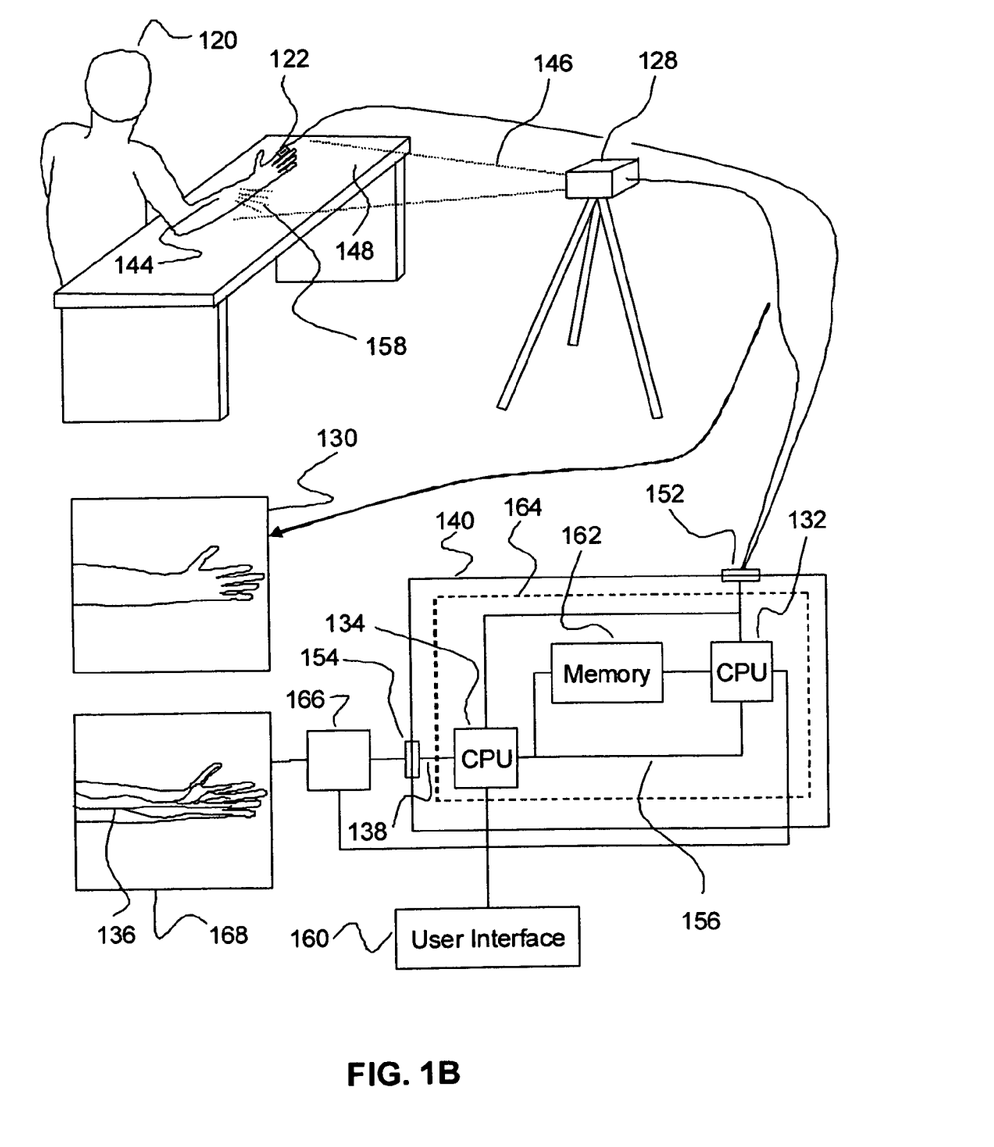
FIG. 1B shows a top level overview of an alternative embodiment with direct timing measurement.

FIG. 1B—Overview of Alternative Embodiment with Direct Timing Measurement

FIG. 1B illustrates a top-level overview of an alternative embodiment of the visualization system or V-system 140 wherein a measurement of the biological function of interest is a separate input. This implements the alternative embodiment of the V-method shown in FIG. 2B.

The only fundamental change vs. FIG. 1A is that the sensor 122 is directly connected to the input interface 152. The decoder 132 is reconfigured to implement the changes shown in FIG. 2B. Consequently, the following elements of FIG. 1A are no longer used and are omitted here:

(a) signal encoder 124
(b) source 126
(c) source encoded output 148 (by virtue of removing the source)

All other referenced elements and interconnections remain as described in FIG. 1A. This description is not repeated here for the sake of brevity. The reader is referred to the discussion of FIG. 1A for further details.

Figure 1C:
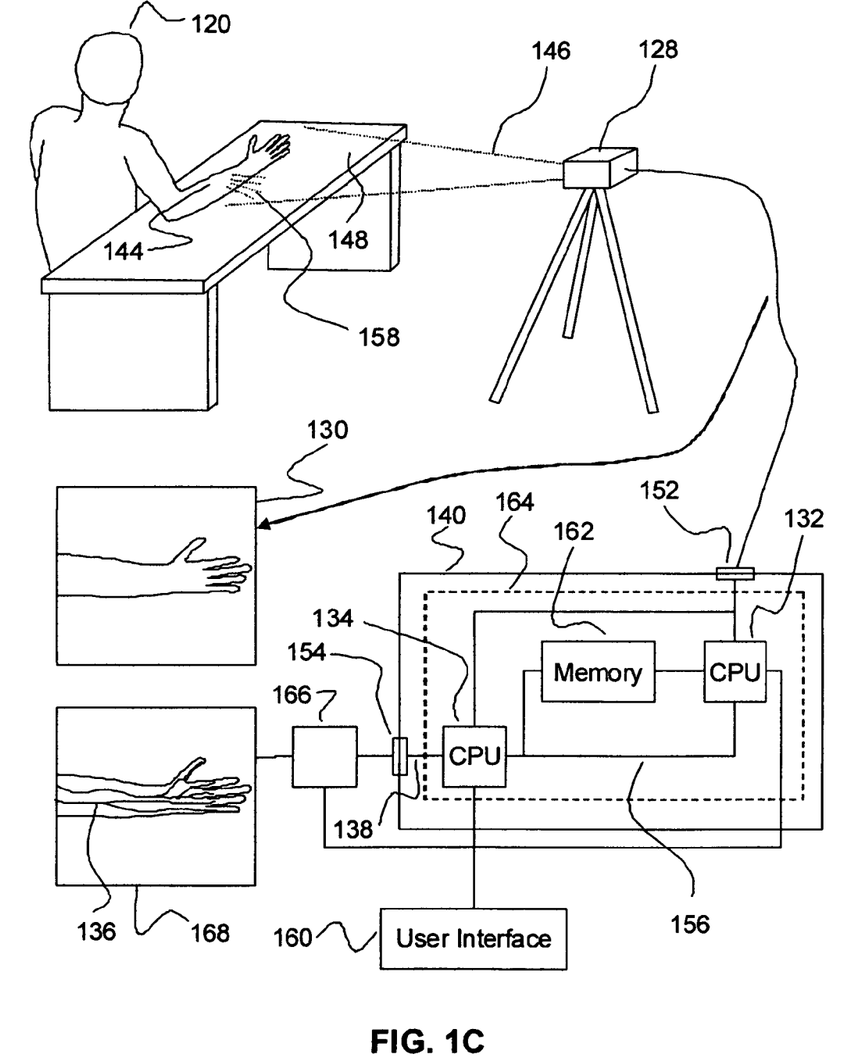
FIG. 1C shows a top level overview of alternative embodiment with un-augmented timing measurements.

FIG. 1C—Overview of Alternative Embodiment with Implicit Timing Measurement

FIG. 1C illustrates a top-level overview of an alternative embodiment of the visualization system or V-system 140 wherein all measurements of the biological function of interest are derived from the image sequence 130, without input or encoding of addition augmentation. This implements the alternative embodiment of the V-method shown in FIG. 2C.

The only fundamental change vs. FIG. 1A is that the sensor 122 and all related elements are omitted. The decoder 132 is reconfigured to implement the changes shown in FIG. 2C. Consequently, the following elements of FIG. 1A are no longer used and are omitted here:

(a) signal encoder 124
(b) source 128
(c) source encoded output 148 (by virtue of removing the source)
(d) sensor 122

All other referenced elements and interconnections remain as described in FIG. 1A. This description is not repeated here for the sake of brevity. The reader is referred to the discussion of FIG. 1A for further details.

FIG. 2A—Process Steps for the Preferred Embodiment

FIG. 2A details steps in the preferred embodiment of the visualization method or V-method 240. This embodiment utilizes an explicit timing reference encoded into the input image sequence 130. Other embodiments which do not thusly encode the timing reference are covered in the following. While steps are nominally shown in sequence, it should be apparent to one normally skilled in the art that some may equivalently be done in parallel or in a different order. Each illustrated embodiment of the method includes, by inference, this and other equivalent substitutions.

To begin with, encode the synchronization 238. To do this, first measure the biological function from which the synchronization timing is to be derived, or measure the sync 242, then determine the timing of this signal and encode the timing 244 so that it may later be recovered. Finally, output the encoding 246 so that it is embedded in the image sequence 130.

Then, collect imagery of the desired area of the patient (including the preceding embedded source), or collect the image sequence 200. To do this, first, acquire images from the patient and source using the imaging systems or acquire image sequence 226. Then store the data 228, and retrieve the data for processing or retrieve the data 230. Note that store data 228 and retrieve data 230 degenerate to a simple data pass-through (null function) in the case of direct real-time processing. Or they may equivalently be bypassed to process on-line 248.

Next, identify the timing reference 202. To do this, first identify the area of the image containing the source for the encoded signal or select the source area, 204. Next, since this embodiment uses a binary modulation, detect transitions in the source or detect transitions 206. In this embodiment, that is all that is required for decoding, since each transition indicates the start of a pulse cycle.

Next, collect the intensity of a plurality of areas in each image or collect intensities 250. First, track the patient motion 210. Then, use this information to select a plurality of samples that are fixed relative to the patient or select sample areas 212. In applications where the patient does not move enough to degrade the demodulation result, these steps degenerate to selecting a set of areas that are fixed in the image.

Next, demodulate evidences of the patient's biological function from the image sequence, or demodulate 252. The first step of this is done per image, rather than per image area: Determine which timing transition (See 206) occurred immediately before each frame was sampled, and determine the sample time of the image frame relative to that transition (the delay between the transition and the frame time), or measure frame relative phase 208. This establishes the output timing reference for each frame or timing reference 156

Subsequent demodulation steps are repeated for each selected area or for each area 214. This is illustrated by a loop control block. The steps to the right are repeated per area.

First, average the pixels in that area in each frame and collect those averages across the image sequence, or average pixels 216. Then, create a composite waveform or create composite 218 by reordering the averages according to the relative timing 156. This composite merges all of the data into a single phase-registered cycle of the periodic function. Then remove any part that is not modulating with the pulse or remove constant part 220, and smooth the composite waveform, or smooth 222. Then, using other methods well known to one normally skilled in the art, such as cross correlation, determine the modulation amplitude and phase or characterize the modulation 224 in that area.

The remaining steps are referred to in the aggregate as assemble output 256. This includes building and displaying the output map.

As areas are processed, assemble the results for the areas into a spatial map or build spatial map 232. This spatial map is the fundamental output of the method. By observing this map using conventional means, one is able to observe anatomy and biological function that are not otherwise evident in the raw images using such means. The intent of this method is to create data which may be examined through a variety of conventional means, rather than to recommend a specific display process. The display method shown here is for illustrative purposes, and is not to be construed as limiting.

To form a display, first, assign map values to display brightness and color or assign colors 234. Then, display these values on a suitable device or monitor, or display result 236.

Figure 2B:
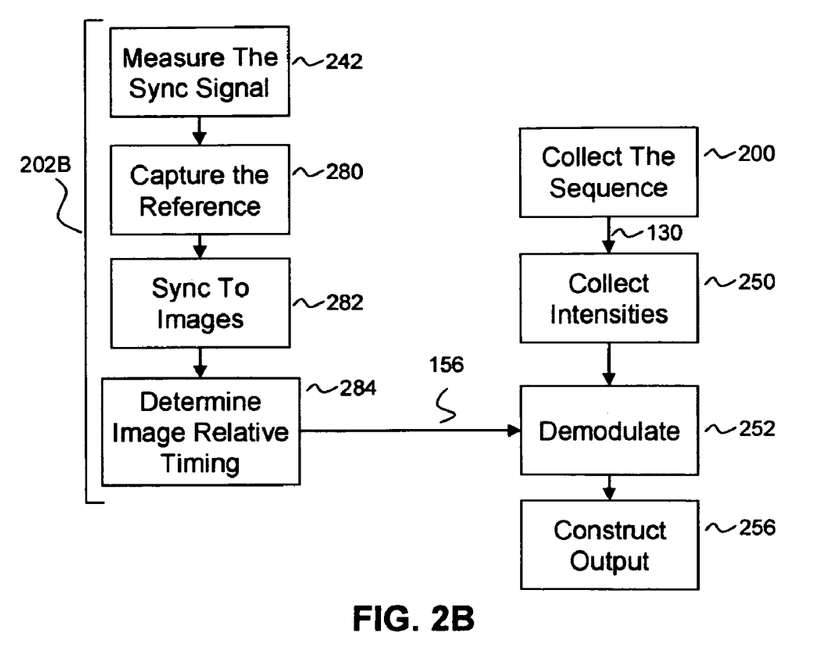
FIG. 2B shows an alternative process embodiment with direct measurement.

FIG. 2B—Alternative Process Embodiment with Direct Measurement

FIG. 2B details steps in an alternative embodiment of the visualization method or V-method wherein the timing reference is derived from direct measurements of the biological function of interest rather than from encoding the timing of such measurements in the input image sequence 130.

As in the preferred embodiment, collect the image sequence 200 feeds the image sequence 130 into collect intensities 250, which feeds into demodulate 252. The output of demodulate 252 feeds into construct output 256. The details under each of these blocks remain as previously shown.

The differences occur in an alternative embodiment of identify the timing reference 202B, which uses separate input data, rather than data separately encoded into the image sequence 130, to create the timing reference 156. This alternative embodiment consists of the following steps.

First measure the biological function from which the synchronization timing is to be derived, or measure the sync 242. Next, capture this measurement or capture the reference 280. Then, synchronize this data to the image sequence so that the relative timing can be determined, or synchronize to images 282.

When this data is captured in a manner that is implicitly synchronized to the image sequence, such as capturing on a synchronized data track, no explicit synchronization is required. This is the preferred method. In other cases, relative synchronization must be provided explicitly. As per usual practice, such explicit methods might include time tagging and delay reconciliation, or other equivalents. Capture the reference 280, as used here, is intended to include such common variations, rather than to select among them.

Then determine timing 284 produces the timing reference 156. To be consistent with all other details of the preferred embodiment, the timing signal is the time since the last rising edge of the pulse for each image.

Figure 2C:
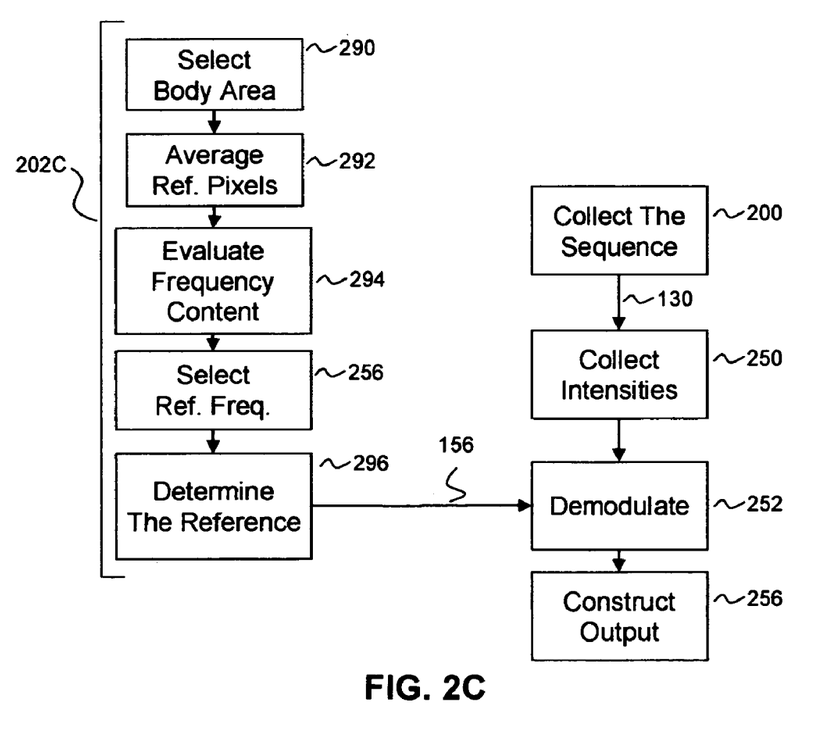
FIG. 2C shows an alternative process embodiment with un-augmented timing measurements.

FIG. 2C—Alternative Process Embodiment with Implicit Timing Measurement

FIG. 2C details steps in an alternative embodiment of the visualization method or V-method wherein the timing reference is derived implicitly from the image sequence 130.

As in the preferred embodiment, collect the image sequence 200 feeds the image sequence 130 into collect intensities 250, then into demodulate 252. The output of demodulate 252 feeds into construct output 256. The details under each of these blocks remain as previously shown.

The differences are in an alternative embodiment of identify the timing reference 202C, which derives the timing directly from the captured image sequence of the patient. This alternative embodiment consists of the following steps.

First, select an area containing pixels on the patient's body or select body area 290. Then average the selected pixels in each frame together or average the reference 292. Then, look at this average for each frame across the image sequence 130 to evaluate the frequency content 294. Next, identify the peak frequency content at a frequency consistent with the biological function currently being observed, or select reference frequency 216. Finally, use the frequency and phase of that signal to determine the timing reference, or determine the reference 298. This produces the timing reference 156 which is then processed as in previous discussions.

Figure 3:
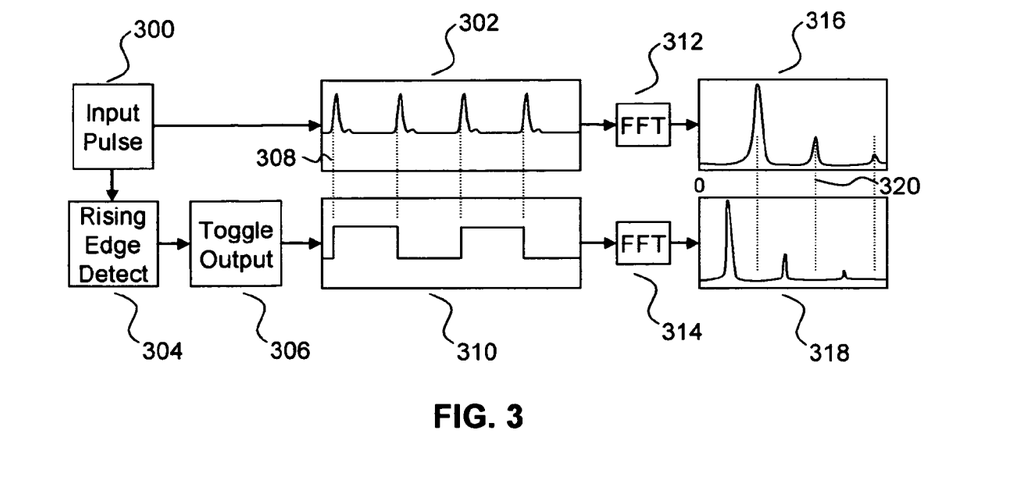
FIG. 3 illustrates the function of the preferred embodiment for encoding the reference timing in the image.

FIG. 3—Encoding Biological Function Timing in the Input Image

FIG. 3 illustrates the function of the preferred embodiment of the reference timing encoding as processed in FIG. 2, when used to image a patient's heart beat or pulse. The input pulse waveform or input pulse 300 is measured by sensor (122 in FIG. 1). This waveform is show graphically as the pulse waveform graph 302. First, detect rising edges in the pulse waveform or rising edge detect 304. Then toggle a digital output at each rising edge or toggle output 306, providing the signal encoding. The output of this step is shown graphically as encoded signal graph 310. The pulse waveform graph 302 and encoded signal 310 are drawn so that points at the same horizontal position occur at the same time. Timing marks 308 illustrate points in the two plots that occur at the same relative phase of the patient's pulse, highlighting the relationship between the signals.

Frequency transforms 312 and 314, and the preceding and following graphs, are included here only to aid in illustrating function. They are not part of the encoding process illustrated here.

The pulse frequency graph 316, and the encoded signal frequency graph 318, show the frequency content of the signal and encoding (for positive frequencies). Corresponding frequencies are shown at the same horizontal position. Alignment lines 320 aid in observing that the encoded signal has no significant content at the frequencies contained in the pulse waveform.

Figure 4:
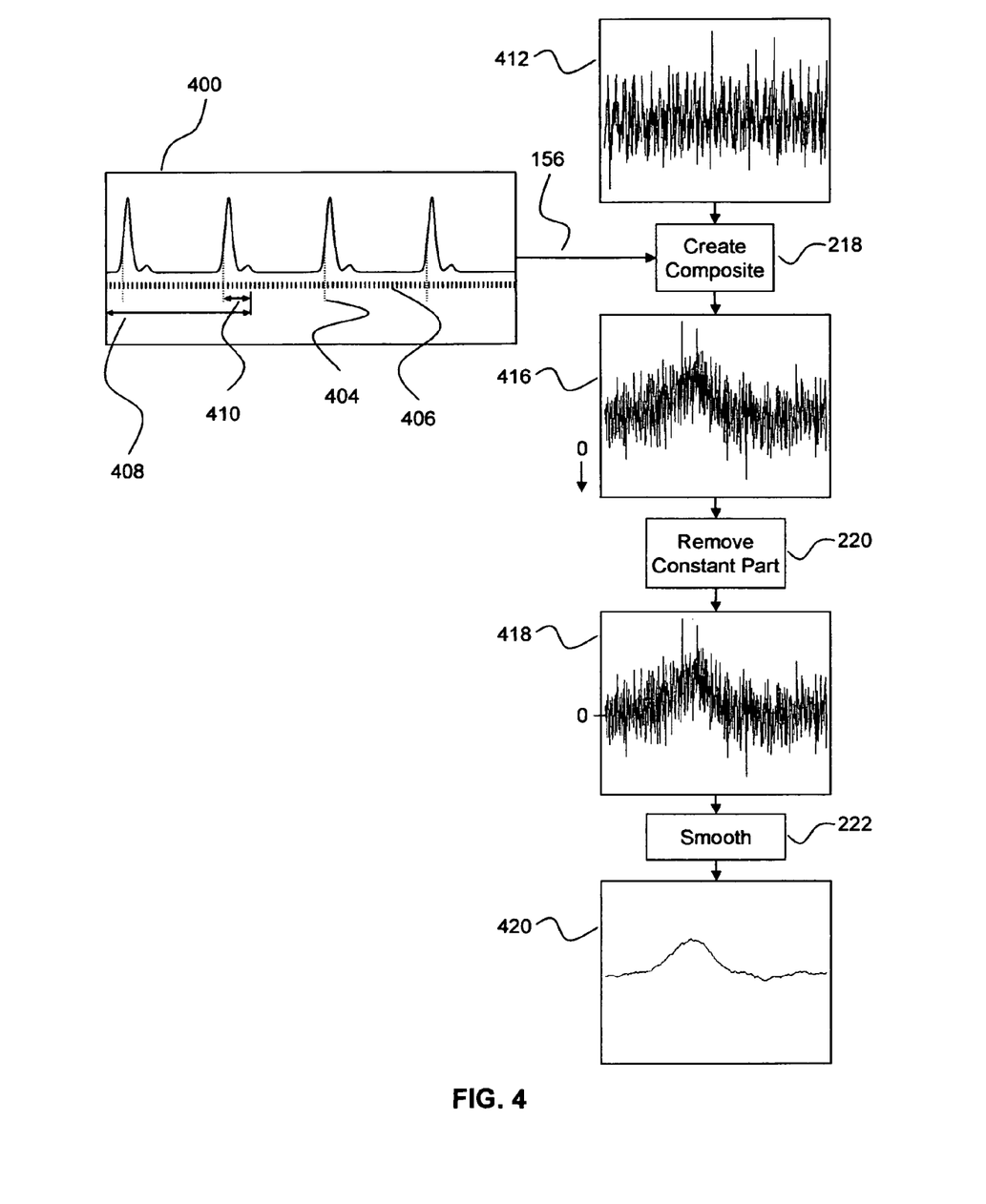
FIG. 4 illustrates the functions of demodulation using a composite waveform.

FIG. 4—Demodulation Via Composite Waveform

FIG. 4 illustrates the effect of determining the composite waveform for demodulation. This illustration shows the specific case of demodulating the imagery according to the patient's heart beat or pulse in the preferred embodiment, but this should be construed as illustrative rather than as restrictive.

The pulse graph 400 provides a notional illustration of the patient's pulse which is measured by the reference sensor (FIG. 1, 122). Phasing marks 404 show the position of the leading edge of each pulse. Frame timing marks 406 show the time at which each image frame in the image sequence is sampled. To avoid over cluttering the figure, the frame rate shown is somewhat lower than typical cameras provide. Again, this is intended as illustrative, not restrictive.

The absolute sample time for an arbitrarily selected frame is shown by the absolute timing arrow 408. The corresponding relative time for the same frame is shown by the relative timing arrow 410. This timing reference 156 provided to the next step.

The intensity in one area of the image across the frames of the input sequence is shown notionally in the input intensity graph 412. This graph shows data with a signal-to-noise ratio (SNR) of one, but this is intended as illustrative not restrictive. Note that the time scale in the plot is longer than the scale for the pulse graph 400.

The input intensity graph 412 does not show anything useful, correctly reflecting the fact pulse modulation is not directly visible in the input sequence. Making such modulation visible is a highly unobvious consequence of the processing described here.

Create composite 218 uses the pulse timing to reorder frames from the input intensity, realigning each sample according to its relative timing as shown by the relative timing arrow 408, to produce a high temporal resolution image of a single cycle of the any modulation in the selected area of the image that is consistent with the patient's pulse, or the composite waveform 416.

Remove constant part 220 gets rid of the portions of the input that do not modulate according to the pulse timing reference. The result is shown in modulating part 418.

Smooth 222 removes the content of the modulating part 418 that is not consistent with reasonable pulse-dependent waveforms producing a smoothed waveform 420. In this example a simple box-car filter was used, illustrating that techniques well know to those skilled in the art are sufficient. The high degree of temporal over sampling in the composite waveform 416 makes this possible.

Observe that the shape of the demodulated waveform does not match the sensed reference pulse. This is generally the case. It cycles at the same period, but has a somewhat different shape due to the local characteristics of the blood flow, hence the value of the waveform shape as a diagnostic tool.

Note that the time scale of the pulse graph 400, input intensity graph 412, and the composite waveform 416 are all different, while the relative scales of the composite waveform 416, modulating part 418, and smoothed waveform 420 are all the same. The relative scales shown are illustrative, not restrictive.

Figure 5:
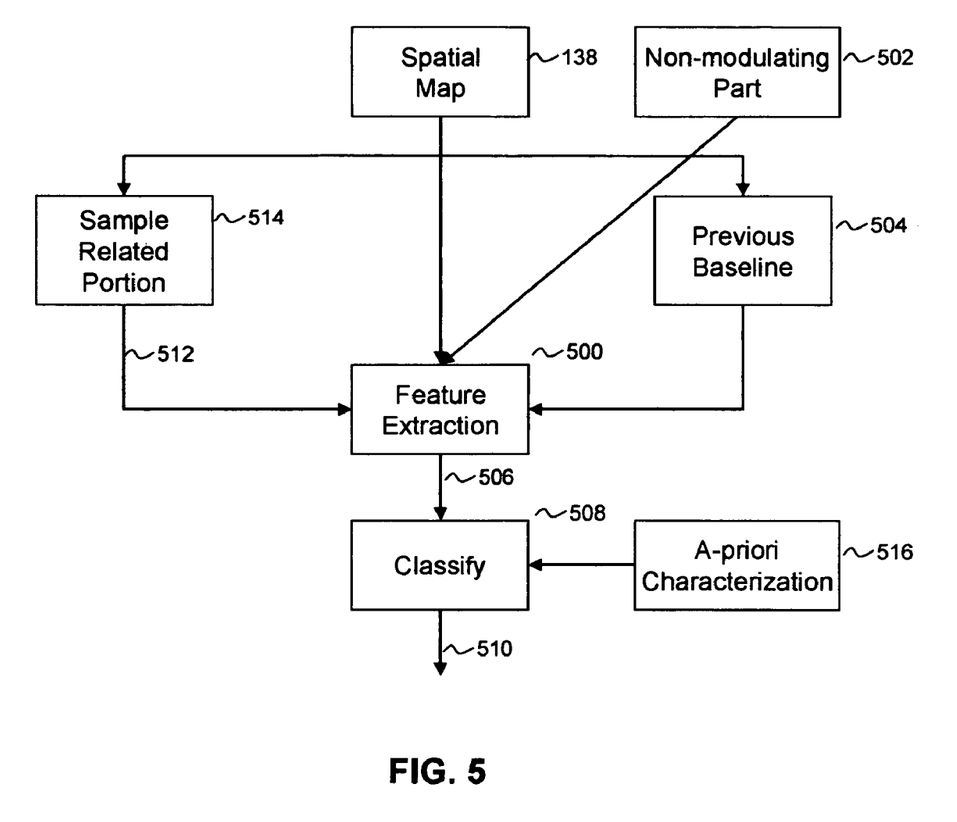
FIG. 5 shows alternative embodiments of further augmenting the spatial map.

FIG. 5—Alternative Additional Processing Steps

FIG. 5 illustrates additional processing steps of an alternative embodiment that may be used to further enhance the spatial map 138 in specific circumstances where this is desirable. In particular, the steps shown utilize the temporal modulation measured by this method. It is presumed that one normally skilled in the art would apply other conventional enhancements to the map for processing or display within the scope of this method.

Feature extraction 500 accepts as input modulation map 138 possibly augmented by any combination of the following:
 a) a corresponding map of the constant or non-modulating part of the time series for each area that was removed during demodulation or non-modulating map 502,
 b) at least one previously sampled baseline map 504 including at least some of the same features,
 c) a corresponding map of a related portion of the anatomy, including without limitation a reversed map of the opposite side of the patient's body 512 as determined by sample related portion 514.

It derives additional parameters, or features, correlated to phenomena of interest. These are added to an augmented map 506 which includes at least one of these features and which may also include all or part of the measurement in the input map 138.

A further step accepts as input this augmented map 506 and performs a classification 508 step based on predetermined combinations of one or more feature values that are predetermined to be consistent with various conditions of interest, or a priori data 516. The results of this classification are embedded, possibly combined with all or some of the input features, are included in a further augmented map 510.

In the degenerate case, this function acts simply acts as a pass through. This is the case in the preferred embodiment.

OPERATION OF INVENTION

Theory of Operation

The fundamental principle is that periodic biological functions and their related anatomy that cannot be seen in imagery using typical means, can nonetheless be made visible by demodulating the image sequence according to the timing of that biological function. In particular, vascular structure and the function of that structure becomes observable when demodulated according to the patient's heart beat.

In static imagery, the signal to clutter ratio is typically too small for these modulating features to be picked out. Their contrast is smaller than that of the background clutter. However, demodulating the image sequence in this manner suppresses the background while enhancing the desired signal. It leaves only the portions of the image that modulate in cycle with the phenomena of interest.

This makes the modulating features observable. But, even more information may be obtained.

By demodulating the entire image of the patient using a single timing reference, not only is the signal-to-noise ratio (SNR) improved, relative phase information is available across the image. In the case of heart-beat, this relates to the pressure wave of each heart beat traveling through the vascular system. It maps the course of the blood flow.

In some cases the reference modulation can be detected directly from the image itself. For example, looking for the frequency and phase of a stable heart beat.

In others it is desirable to use an explicit measurement of the reference. For example, consider using a pulse measurement to demodulate images of a varying heart beat. The obvious method is to separately record a pulse monitor. But, one must then synchronize this data with the input imagery. Another alternative, the preferred embodiment here, encodes the timing of the external reference without influencing the measurements of interest, but so that it can be decoded from the same image sequence.

It is expected that clinical testing will demonstrate that different disease modalities affect the relative amplitude, phase, and shape of the pulse waveform as it progresses through the affected area. For example, it is speculated that cancer will tend to produce a lower entropy waveform, showing less active arterial pumping than surrounding areas that otherwise indicate the same volume of blood flow.

Regardless, it is clear that the increased feature space available with such measurements would make it far more difficult to spoof a biometric system. Some existing systems look for a pulse and for veins in a subject's fingertip (although they do not measure spatial variations in the pulse). A counterfeit including a static vein pattern with a fingertip pulse simulator could spoof such a system. If the method described here were used, the counterfeit would further require modulating the veins themselves, and faking pulse wavefront progression (change in phase) along the length of the veins during a pulse cycle. This is far more difficult to counterfeit.

The intent of the current invention is to produce a spatial map showing such modulations across an image. It is not to determine the final method or mechanization of processing of displaying this map. It is to produce an input where this is conveniently done using conventional techniques for the processing and display of multivariate images, which would not by themselves be able to reveal the modulations.

Application to other biological functions and sensors has received less speculation and investigation at this point, although some are mentioned under alternative embodiments.

OPERATION OF INVENTION

Preferred Embodiment

A living creature or patient 120 (FIG. 1), exhibits some periodic biological function. The objective is to be able to visualize, using imaging equipment or camera 128, subtle changes across the patient that modulate according to rhythm of this function. The difficulty is that these changes are not directly observable by the camera 128. The operations discussed here correct this.

The remainder of this operational discussion focuses upon the special case where the periodic biological function of interest is the patient's heart beat or pulse, where the pulse is used to highlight vascular structure and to characterize the blood flow through it in novel ways, and where the patient is observed using some form of infra-red camera. This focus is strictly for purposes of illustration and clarity, to avoid unnecessarily cluttering the discussion, and is not intended as restrictive.

First, the camera 128 is placed so that the area that we wish to observe of the patient's body, in this case an arm 144, is within the camera's field of view or FOV 146. In a biometric system the FOV might be aligned to cover the face or a finger tip.

The camera 128 is placed and configured so that it is able to observe IR emissions from the patient that modulate in time with the pulse or the signal from the patient 158.

Camera Configuration

There is an inherent trade between resolution and sensitivity, so the FOV should not arbitrarily cover more than the area desired. For example, it may be desirable to have multiple pixels across the smallest blood vessel which we wish to see. While one will generally detect a signal even when the resolution is somewhat less than desired, the signal amplitude will be degraded. Ideal resolutions for different cases remain to be determined.

Normal practices for high thermal resolution imaging may beneficially be followed, but this can be somewhat different than normal practice for other medical imaging. First, it is not important to maintain absolute mappings of camera readout to body temperature, because any constant part will later be suppressed (FIG. 2, 220). Here, it is preferred to have more gray levels across the patient, to be able to see smaller variations (note that this often looks worse on a display). This method utilizes levels that would not be useful for other purposes, so this extra adjustment is not typically done. This will bring out the sensor random noise, but that is OK. The gains may be set so that the random noise covers at least one gray level one-sigma to limit quantization error. Going beyond two gray levels typically is not helpful. The dynamic range may also be set to the keep the desired area of the patient within the linear range of the detectors (by photon flux, not by temperature), with 10-15% margin.

Again, as per normal practice in high thermal resolution imaging, the camera non-uniformity compensation (which adjusts for small differences in the gain and offset response of different pixels in the array), may be calibrated to the range of the patient's body. A two-point calibration may be preferred. This calibration typically uses two temperature sources, one at slightly above the highest temperature on the arm and the other at slightly below the lowest. This is more restrictive than typical medical imaging practice, again, because this method may utilize smaller variations. This calibration is supported directly by many cameras, and when not, by many image acquisition packages.

Camera focus issues are not substantially different than for conventional imaging, other than to allow for extra depth of field from sub-skin surface imaging. Typically this requires no special consideration.

Normal practices for precision radiometry and image frequency analysis may beneficially be employed in that care should be taken to remove harmonic sources from the environment. Typical culprits include feed through from lighting (in some bands), oscillations induced by running ventilation, vibrations from equipment (altering reflections within the area), and things like computer cooling fans. In the latter case the fan acts like a chopper intermittently allowing the outside world to see portions of a hot power supply, which can create a variety of odd harmonics when aliased down to the camera sample rate.

It is simplest and is recommended to use a camera which is electronically shuttered, where all pixels in each frame are integrated over the same time window. Interlaced cameras, and cameras where each pixel is sampled for the same length of time but immediately before it is output, are other typical options. In these cases extra care may be required to allow for the lack of time synchronicity. Various methods known to those skilled in the art of using such cameras for precise analysis of fast motion can be used to compensate for the differing time delays where needed.

Reference Timing

In the preferred embodiment, the reference timing for the patient's pulse is mixed with the signal from the patient 158 in FIG. 1, that is sensed by the camera 128. This is done by the V-device 142, operating as follows.

A reference sensor or sensor 122 measures the patient's pulse. In this example, the sensor 122 is substantially in contact with the patient 120, but this should not be construed as limiting. Sensors which do not require body contact may equivalently be used.

The sensor 122 feeds into to a signal encoder 124 which extracts timing data from the sensor measurement and creates a signal encoding this timing, such that the timing of the original measurement from the patient can be extracted from this encoding. This signal is applied to the attached signal source or source 126, which produces the source encoded output 148 that is sensed by the camera 128.

An appropriate pulse sensor can easily be assembled by one normally skilled in the art. Less than 10 minutes of internet searching provided an appropriate schematic for a near-IR optical transmission type device. Electrical sensors would also be suitable. The pulse is thresholded and then encoded. For production use, some care should be taken to automate the thresholding, so that it produces a consistent edge at the same positions in each pulse, even as the pulse amplitude and frequency change. Such methods are well know to those skilled in the art, and are not detailed here.

The signal encoder 124 may cause the encoded output 148 to be nominally orthogonal, mathematically, to signals from the patient 158 as captured directly by the camera 128. This provides, in effect, an independent input channel through the existing optical input to the camera 128, whereby a timing reference is placed in the image without interfering with the signal from the patient 158.

A suitable encoding method is shown in FIG. 3, where a digital output is alternated at the rising edge of each pulse, or toggle output 306. This is easily accomplished using a simple program in a commercial micro-controller. The encoded pulse frequency graph 316 shows that the encoded signal does not overlap with harmonics of the heartbeat shown in the pulse frequency graph 318. As previously stated, they are nominally orthogonal to each other. This prevents the encoded signal from interfering with the signal from the patient 158.

Returning to FIG. 1, the source 126 has thus far been implemented by a mechanical chopper. A mechanical arm is attached to a servo motor and moved in and out of blocking a thermal source on alternate pulse beats, where the arm and source have relative contrast with each other. A penlight is an adequate thermal source. A micro controller does the encoding and controls the pulse-width modulated drive to the servo motor using methods well known to those skilled in the art. The prototype used an Atmel AT-Tiny 12 microcontroller, directly driving a model-airplane type servo directly from one of the output pins. Information on driving these servos can be somewhat difficult to locate. The important parameters are that positive pulse widths from about 0.5 to 2 ms typically cover the whole range of motion, and the pulse repetition rate must be high enough to avoid instability and vibration (typically >100 Hz).

More recent innovations have produced micro black-body thermal sources with sufficient temporal response to serve directly as the modulated source. The MIRL 8-300 from Electro Optical Components, Inc in Santa Rosa Calif. is one such device. Previous devices did not change temperature fast enough (particularly cooling) to provide adequate modulation. These new devices obviate the need for a mechanical chopper when the encoded signal from the micro controller is fed through a suitable amplifier directly into them.

This source 126 is placed within the FOV 140 of the camera so that it may be seen as imagery of the patient is captured. The source 126 and encoding is constructed, particularly in choice of waveband and temporal content, so that the source encoded output 148 is visible to the camera 128 and does not excessively interfere with the signal from the patient 158.

Image Capture and Sync

The image sequence 130 from the camera 128 is passed via an input interface 152 to a reference processor or decoder 132 of the V-system 140. The decoder 132 extracts the timing data placed into the images by the V-device 142, thereby producing a timing reference signal or timing reference 156.

The method for extracting the timing reference is illustrated in FIG. 2A. First collect the image sequence 200.

Next, identify the timing reference 202. To do this, first identify the area of the image containing the source for the encoded signal or select the source area, 204. Next, since this embodiment uses a binary modulation, detect transitions in the source or detect transitions 206. In this embodiment, that is all that is required for decoding, since each transition indicates the start of a pulse cycle.

The source area could be selected manually. However, a variety of methods well known to those skilled in the art of automated image processing will suffice to automatically locate it wherever it is placed. This is simple since it is clearly distinct from the patient being observed.

Depending upon the configuration of a moving arm source, it is sometimes desirable to track the arm in the image, in order to detect transitions. With low grade servo motors the time at which the arm begins to move on each cycle is a more accurate measure of the input timing than the time at which it crosses any particular pixel. For modulated beacons, such as the pulsed black body, it is sufficient to look for sudden rises or falls in the observed temperature across the source.

Demodulation

Returning to FIG. 1, the timing reference 156 feeds, along with the image sequence 130, into the demodulation processor or demodulator 134 which produces a spatial map or map 138. This map shows the local presence in different portions of the image of modulating signals from the patient 158.

The method of creating this map is presented in flow chart form in FIG. 2A. To start, collect the intensity of a plurality of areas in each image or collect intensities 250. The key is that these areas should be substantially fixed on the patient. When the patient is substantially stationary, fixed areas in the image suffice.

The following rule of thumb helps to determine whether patient motion matters in a particular situation: Determine the thermal gradient observed across the patient's body. Find the maximum levels in gray levels per pixel. Multiply it by the patient motion observed over a frame time, in pixels per frame. This will ballpark the magnitude of the induced noise from uncompensated motion. This may beneficially be limited so that it is not be much larger than the signal. Also note that the noise will not be white: it will be a function of the background clutter and the noise spectra, producing harmonic spikes which may beneficially be avoided here.

Several methods are available to reduce the effects of patient motion:

(a) limiting patient motion, (b) excluding portions of the image where thermal gradient are particularly severe (such as edges of the body near high-contrast backgrounds), (c) stabilizing the image sampling relative to the patient motion, and others known to those skilled in the art. Select an appropriate balance. FIG. 2A presumes an option including (c): First, track the patient motion 210. Then, use this information to select samples that are fixed relative to the patient or select sample areas 212.

Next, measure the relative phase 208 of each frame relative to the timing reference. This is illustrated in more detail in FIG. 4.

The phasing marks 404 on the pulse graph 400 show the leading edge of each pulse. Find the pulse immediately preceding each frame. The relative phase for a selected frame is shown by the relative timing arrow 408. This is the timing reference previously described.

The intensity in one area of the image across the frames of the input sequence is shown notionally in the input intensity graph 412. This data shows a signal-to-noise ratio of one. To draw something useful out of this data, create composite 218 re-maps the data so that the ordinate axis is replaced by the relative timing for each frame. The result is a composite waveform 416 of a single cycle of any patient signal modulating in sync with the pulse waveform. Remove constant part 220 and smooth 222 respectively remove portions of this signal that are not modulating, or that are not sufficiently well sampled to represent true signal vs. noise and interference, producing a smoothed waveform 416. Any of a variety of techniques well known to those skilled in the art of filtering irregularly spaced samples may be used for smoothing. This example shows a simple box car filter. It is not the best performing method, but it is simple and is adequate here. This discussion is intended to cover other equivalent methods, and improvements well known to those normally skilled in the art.

In general, as shown, the demodulated waveform at any particular point in the image does not match the shape of the pulse waveform used to produce the reference timing. The period is the same, but the shape is different, based upon the local blood flow, hence the value of the waveform shape for diagnostic purposes.

One benefit of this particular demodulation method in this case is that it works well when the pulse is not completely stable. In general, the relative position of the pulse waveform varies more than the shape of the waveform, as observed at one point on the body. By creating the composite in this manner the pulse jitter does not substantially affect the reconstructed waveform.

Returning to FIG. 2, characterize the modulation 224 and then collect it across the image in build spatial map 232. The preceding sequence is repeated for each area in process areas 214.

Output

When the map is completed, assign colors 234, and generate display 236 of the result. The map itself is a useful and non-obvious result. The objective of this method is not to establish a recommended display method or mapping process that is adequate for all purposes. Rather, it is to produce an output where data that was otherwise hidden has been rendered into a multivariate two-dimensional map, which may then be displayed, processed, and explored through conventional means.

Returning to FIG. 1, A user interface 160, is used to control the display mapping 166, driving a display 168.

Hardware Required for Implementing the Method

This preferred embodiment of this method is constructed so that it can be implemented with an available infra-red camera, computer, and interfaces, requiring only the V-Device 142 to encode the pulse synchronization. All other functions can be handled by software on a common desktop computer. In particular, for ease of initial configuration, data may be captured using tools available with the camera, and then processed offline.

Alternative Embodiments

A reader normally skilled in the art will certainly see many variations possible in the mechanization and approach. The following discussion highlights only a few of them, and is intended as illustrative, not restrictive.

First, two alternatives for providing a timing reference (FIG. 1, 156) have already been discussed. One uses a more conventional approach, and captures the patient's pulse separately (FIGS. 1B, 2B). The other identifies the timing reference directly from the imagery (FIGS. 1C, 2C).

Separately capturing the pulse proved inconvenient for prototyping this method, because of synchronization issues. While available tools could capture the image and the pulse data for off-line processing, the same tool would not capture both. This required some method of synchronizing the two data streams. Recall that the pulse is capture to provide the timing reference for the images, so this is critical. Many typical methods are available and well known to those normally skilled in the art of processing telemetry data, including time-tagging. However, encoding the information in the imagery proved simpler. In an implementation with more customized hardware this is not necessarily an issue.

Decoding the timing reference directly from the imagery, without separate measurement or encoding, is viable under some conditions. The biological function of interest must be stable enough over a sufficiently long observation period to build the decoded signal SNR sufficiently to provide the desired time accuracy. When this condition is met, the separate encoder or reference capture can be bypassed. However, using a separate encode may still improve results.

The most obvious hardware implementation alternatives relate to what is included with what. Referring to FIG. 1, the decoder 156, demodulator 134, memory 162, display mapping 166, user interface 160, and display 168, are identified here as separate elements. They may equivalently all be implemented using a conventional single or multi-processor desktop computer system.

Looking in a different direction, the preceding discussion has focused primarily on use of infra red imagery for measuring modulations with the pulse. Another alternative is to use a flashing light in a transmissive mode, as in some biometric systems. We can then use the method discussed here to extract pulse dependent features, highlighting not only the vascularization, but the phase of the blood flow through it. This is a far more complex and difficult to counterfeit pattern than veins alone.

CONCLUSION RAMIFICATIONS AND SCOPE

Periodic biological functions and their related anatomy that cannot be seen in image sequences using typical means, can nonetheless be made visible by demodulating the image sequence according to the timing of that biological function, as per the described method, device, and system. In particular, vascular structure and the function of that structure become observable when demodulated according to the patient's heart beat. Two-dimensional imaging of such modulations represents a fundamentally new line of thought in medical imaging, with substantial historical momentum leading away from it, and away from recognizing the highly non-obvious benefits obtained.

The invention has been described with reference to the preferred and certain alternative embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method of producing one or more images of body structure and function related to a periodic biological function of a subject comprising steps of:
    (a) collecting at least one image sequence showing at least part of said subject's body, where an image includes a plurality of spatially-defined pixels and the image sample rate is greater than the temporal frequency of said biological function,
    (b) sensing a reference frequency for the periodic biological function relative to said image sequence,
    (c) demodulating, or removing the non-modulating part of, intensity variations in a plurality of image areas over time across said image sequence according to said reference frequency,
    (d) characterizing the modulation produced by said biological function that is present in each image area, and
    (e) producing at least one spatial map or image, of the characterized modulation of the observed body structure and function.

2. The method of claim 1 wherein step (b) comprises sensing a reference frequency of said subject's heart beat or pulse.

3. The method of claim 2 wherein step (a) further comprises collecting passive images without explicitly radiating said subject.

4. The method of claim 3 wherein step (a) further comprises collecting passive images including at least one color that is substantially beyond visible wavelengths into the infrared wavelengths.

5. The method of claim 2 wherein step (b) further comprises sensing said reference frequency for said heart beat or pulse from said image sequence, rather than from separately captured data.

6. The method of claim 5 wherein step (b) further comprises augmenting said image sequence through steps comprising:
    (b1) measuring said heart beat or pulse through means other than said image sequence,
    (b2) encoding and modulating, based upon the measurement of step (b1), a separate source configured to be visible in said image sequence,
    (b3) decoding the effects of said source from said image sequence, thereby inferring said reference frequency for heart beat or pulse timing relative to said image sequence.

7. The method of claim 5 wherein step (c) further comprises steps of:
    (c1) sensing a nearest start of a pulse cycle occurring substantially before the collecting of each said image, as determined from said reference frequency,
    (c2) determining, based upon the nearest start of the pulse cycle the time phasing within the current pulse cycle at which each frame was sampled,
    (c3) re-ordering, according to said time phasing, the observed values for each image area in each image across the image sequence, whereby the data from multiple pulse cycles are formed into a composite representation of a single pulse cycle,
    (c4) removing any constant part across each cycle,
    (c5) smoothing said composite representation to be consistent with reasonable observed waveforms.

8. The method of claim 5 wherein step (b) further comprises sensing said reference directly from the un-augmented images of the subject by steps comprising:
    (b1) averaging together a plurality of pixels in each image,
    (b2) collecting the averaged results across frames into a time series,
    (b3) determining the frequency content of said series,
    (b4) identifying frequencies substantially in agreement with a predetermined expected range of pulse rates,
    (b5) using the phase and frequency of the pulse rates at the frequency thusly identified to produce said reference timing.

9. The method of claim 2 wherein step (e) further comprises producing a map that identifies at least one feature of the demodulated intensity selected from the set comprising
    heart beat waveform amplitude,
    heart beat waveform frequency,
    heart beat waveform shape description,
    a relationship of temporal features of any of the preceding waveforms to non-temporal features,
    difference of any of the preceding waveforms relative to prior baseline measurements, and
    differences of any of the preceding waveforms relative to measurements from a contralateral part of the same subject's body.

10. The method of claim 9 including additional steps of
    (f) identifying combinations of at least one feature of the demodulated signal characteristic of a condition selected from a list comprising: healthy veins, healthy arteries, occlude veins, and diseased tissues,
    (g) encoding said identified combinations in said spatial map.

11. The method of claim 1 wherein step (a) further comprises collecting at least some pseudo images derived from a combination of individual sensors or colors.

12. A computer program embodied in a computer readable medium for causing an apparatus to execute an imaging method, the computer program comprising the procedures for:
    (a) collecting at least one image sequence showing at least part of a subject's body, where an image includes a plurality of spatially-defined pixels and the image sample rate is greater than the temporal frequency of a periodic biological function of said subject, (b) sensing a reference frequency for the periodic biological function relative to said image sequence, (c) demodulating or removing the non-modulating part of, an intensity variation in a plurality of image areas over time across said image sequence according to said reference frequency, (d) characterizing the modulation produced by said biological function that is present in each image area, and (e) producing at least one spatial map or image, of the characterized modulation of the observed body structure and function.

* * * * *